(12) United States Patent
Hallett et al.

(10) Patent No.: US 6,707,048 B2
(45) Date of Patent: Mar. 16, 2004

(54) METHOD AND APPARATUS FOR TREATING AQUEOUS LIQUIDS

(75) Inventors: Ronald C. Hallett, Pickering (CA); Sandro Pecile, Weston (CA)

(73) Assignee: UV Pure Technologies Inc., Scarborough (CA)

(*) Notice: Subject to any disclaimer, the term of this patent is extended or adjusted under 35 U.S.C. 154(b) by 0 days.

(21) Appl. No.: 09/973,715

(22) Filed: Oct. 11, 2001

(65) Prior Publication Data

US 2003/0071224 A1 Apr. 17, 2003

(51) Int. Cl.[7] ................................. G01N 21/01
(52) U.S. Cl. .................... 250/431; 210/748; 250/432 R
(58) Field of Search ........................... 250/431, 432 R, 250/433–438; 210/748

(56) References Cited

U.S. PATENT DOCUMENTS

| | | |
|---|---|---|
| 3,016,721 A | 1/1962 | Davis |
| 3,138,708 A | 6/1964 | Ellner et al. |
| 3,182,191 A | 5/1965 | McFarland et al. |
| 4,002,918 A * | 1/1977 | Graentzel ............... 250/431 |
| 4,017,734 A | 4/1977 | Ross |
| 4,831,268 A | 5/1989 | Fisch et al. |
| 4,922,114 A | 5/1990 | Boehme |
| 4,948,980 A | 8/1990 | Wedekamp |
| 5,001,938 A | 3/1991 | Downie |
| 5,023,460 A | 6/1991 | Foster, Jr. et al. |
| 5,120,450 A | 6/1992 | Stanley, Jr. et al. |
| 5,133,945 A | 7/1992 | Hallet |
| 5,227,140 A | 7/1993 | Hager et al. |
| 5,240,675 A | 8/1993 | Wilk et al. |
| 5,247,178 A * | 9/1993 | Ury et al. ............... 250/438 |
| 5,266,280 A | 11/1993 | Hallet |
| 5,401,474 A | 3/1995 | Hager et al. |
| 5,413,768 A | 5/1995 | Stanley, Jr. |
| 5,440,131 A | 8/1995 | Hutchison et al. |
| 5,501,843 A | 3/1996 | Peterson |
| 5,505,912 A * | 4/1996 | Hallett .................... 422/186.3 |
| 5,528,044 A | 6/1996 | Hutchison |
| 5,612,001 A | 3/1997 | Matschke |
| 5,614,151 A | 3/1997 | LeVay et al. |
| 5,635,133 A | 6/1997 | Glazman |
| 5,780,860 A * | 7/1998 | Gadgil et al. .......... 250/432 R |
| 5,834,784 A | 11/1998 | Morgan et al. |
| 5,874,740 A | 2/1999 | Ishiyama |
| 5,874,741 A | 2/1999 | Matschke |
| 5,937,266 A | 8/1999 | Kadoya |
| 6,013,917 A | 1/2000 | Ishiyama |
| 6,022,511 A | 2/2000 | Matschke |
| 6,429,438 B1 * | 8/2002 | Smestad .................. 250/373 |
| 2002/0144955 A1 * | 10/2002 | Barak et al. .............. 210/748 |

FOREIGN PATENT DOCUMENTS

| | | |
|---|---|---|
| DE | 36 24 169 A | 1/1987 |
| DE | 196 17 467 A | 11/1997 |
| DE | 298 02 771 U | 6/1998 |
| DE | 198 07 540 A | 8/1999 |
| WO | WO90/06899 | 6/1990 |
| WO | WO99/58453 | 11/1999 |
| WO | WO 99/58453 * | 11/1999 |

OTHER PUBLICATIONS

PCT/CA 02/01532, PCT International Searching Authority, International Search Report, dated Jan. 17, 2003.

* cited by examiner

Primary Examiner—John R. Lee
Assistant Examiner—Christopher M. Kalivoda
(74) Attorney, Agent, or Firm—Blake, Cassels & Graydon LLP

(57) ABSTRACT

Method and apparatus for treating a pressurized liquid. The apparatus includes pressurized liquid treatment chamber having a window transmissive to UV light; a UV light source outside of the chamber to emit UV light into the chamber; a shaft which extending between inlet and outlet ends of the chamber which turns about a central axis of the chamber; a flexible cleaning member affixed to the shaft and engaging an interior surface of the window; and at least one member extending radially from the shaft into the treatment chamber to disrupt axial flow of water through the chamber.

33 Claims, 5 Drawing Sheets

METHOD AND APPARATUS FOR TREATING AQUEOUS LIQUIDS

FIELD OF THE INVENTION

This invention relates to the treatment of liquids by exposure to ultraviolet (UV) radiation. An aspect of the invention includes monitoring the effectiveness of UV treatment.

BACKGROUND OF THE INVENTION

It is often desirable, even necessary, to treat aqueous liquids, particularly water, so as to ensure its potability.

The treatment of household water, be it obtained from a municipal water distribution system, in which it has previously been treated, or from a well is often desired. A number of approaches has been developed, including the use of filters, distillation, reverse-osmosis, ultraviolet (UV) light, etc.

There are "point-of-use" systems where a user treats the water immediately prior to use, as by pouring water through a filter, e.g., an activated carbon filter.

There are "point-of-entry" treatment systems where the water is generally treated without the active involvement of the user, except for possibly maintaining the system. In a point-of-entry system the water is generally treated prior to release from its pressurized distribution system. The treatment system may thus be located in a household, for example, such that all water passing from the external source of water to be distributed within the household is treated. Sometimes, such a system is located so as to ensure treatment of water that is expected to be consumed, but to leave untreated water to be used for other purposes, such as washing clothes or lawn watering. This cuts down on wear on the treatment system and can improve economies of use.

In any case, UV-treatment is often regarded as a desirable approach for treating water that is to be protected against the presence of microorganisms that might be found therein. It is in the area of pressurized (e.g., point-of-entry) systems that the invention disclosed herein finds use.

A prior art system related to the present invention is described in the specification of U.S. Pat. No. 5,247,178, issued to Ury et al. on Sep. 21, 1993, the specification of which is incorporated herein by reference.

SUMMARY OF THE INVENTION

A broad aspect of the present invention is an apparatus for treating a pressurized liquid in which the apparatus includes:
- a pressurized liquid treatment chamber having an inlet end and an outlet end, the chamber having a window, preferably quartz, permeable to UV light;
- a UV light source outside of the chamber located such that it emits light through the window into the chamber to expose liquid within the chamber to the emitted light and treats the liquid;
- a shaft which extends between the inlet end and the outlet end of the chamber, located to turn about a central axis of the chamber extending between the inlet end and the outlet end;
- a flexible cleaning member affixed to the shaft and extending radially therefrom to flexibly engage an interior surface of the window for cleaning thereof as the shaft turns; and
- at least one member extending radially from the shaft into the treatment chamber to disrupt axial flow of water through the chamber.

In a preferred embodiment, the chamber window is a circular cylinder made of quartz, quartz being permeable to UV light.

The member extending from the shaft disrupts axial liquid flow, i.e., precludes linear flow parallel to the central axis of the cylinder as the liquid travels through the cylinder. This disruption serves to bring water near the center of the tube towards the window bringing it into better exposure to the UV light. This permits a relatively large proportion of the total volume of the cylinder to be occupied by water travelling through the treatment chamber. In the disclosed embodiment, total usable volume is about 90 percent. Alternatively, the amount of the treatment chamber defined by the cylinder that is free to be occupied by the pressurized liquid is at least 50 percent of the total volume of the cylinder; or is at least about 55 percent of the total volume of the cylinder; or is at least about 60 percent of the total volume of the cylinder; or is at least about 65 percent of the total volume of the cylinder; or is at least about 70 percent of the total volume of the cylinder; or is at least about 75 percent of the total volume of the cylinder; or is at least about 80 percent of the total volume of the cylinder; or is at least about 85 percent of the total volume of the cylinder; or is at least about 89 percent of the total volume of the cylinder.

The member that extends radially from the shaft has a surface transverse to the axis, the obverse face of which faces the inlet end of the chamber. In the embodiment detailed below, each such member or "wing" has an obverse face with cross-sectional area of about 8 percent of the inner cross-sectional area of the tubular cylinder. The cross-sectional area of a wing is generally at least about 5, 6, or 7 percent of the inner cross-sectional area of the tubular cylinder. In certain embodiments, the cross sectional area is equal to at least 9 or 10 percent of the area of the cross section of the cylinder, or about 15, or about 20, or about 25 percent of the area of the cross section of the cylinder.

In a preferred aspect, the apparatus of the invention includes, but is not limited to, three pairs of wings, in which the wings are spaced along the shaft. There is thus a first pair of wings (each wing of a pair angularly spaced from the other of the pair) axially located nearer to the inlet end of the cylinder than to the center (mid-plane) of the cylinder, a second pair of wings located nearer to the center of the cylinder than to either of the inlet or outlet ends of the cylinder, and a third pair of wings axially located nearer to the outlet end of the cylinder than to the center to of the cylinder.

Usually, there is at least one member that is located nearer the inlet end of the chamber than the outlet end. If there is a second member, the first and second members are spaced apart from each other. They can be angularly spaced from each other, or they can be axially spaced from each other, or they can be both axially and angularly spaced from each other.

Preferably, the combined cross sectional areas of the obverse faces of the members is at least 30, or at least 40, or at least 50, or at least 60, or at least 70, or at least 80, or at least 90, or at least 100, or at least 150, or at least 200, or at least 250, or at least 300 percent of the area of cross section of the cylinder. In the disclosed embodiment, the area of each wing is about 8 percent and there are six wings for total surface area of about 48 percent. It is thus preferred that the total obverse surface area presented by the wings be at least about 48 percent of the area of cross section of the cylinder.

The degree to which the wings radially extend from the shaft toward the outer tube also affects the degree to which axial liquid flow is disrupted. In the disclosed embodiment, the wings that protrude radially outwardly from the shaft a distance of about ⅓ the inner diameter of the tube. The distance can be between about ⅕ or ¼ to about ⅜ or 5/11, and to some extent depends upon the diameter of the shaft from which the member extends.

The volume of the interior of the cylinder (the total interior volume, i.e., the volume without taking into account displacement of free volume by the shaft, cleaning member, etc.) is typically between about 25 and 200 cubic inches, or between about 30 and 180 cubic inches, or between about 40 and 160 cubic inches, or between about 50 and 140 cubic inches, or between about 60 and 120 cubic inches, or between about 60 and 100 cubic inches, or between about 60 and 80 cubic inches, or between about 60 and 70 cubic inches. In the disclosed embodiment, the volume of the cylinder is about $(\pi \times (1.6/2 \text{ in})^2 \times 24 \text{ in}=)$ 48 cubic inches (about 786.5 cubic centimetres; or about 0.205 U.S. gallons).

As described in greater detail below, the apparatus of the disclosed embodiment operates satisfactorily at a throughput rate of about 10 gallons per minute.

The inner diameter of the cylinder is preferably between about 1 and 3 inches, or between about 1 and 2.5 inches, or between about 1 and 2 inches, or about 1.5 inches.

The preferred length of the cylinder is between about 6 inches and about 3 feet, or between about 1 foot and 2.5 feet, or between 1.5 feet and 2.5 feet, or about 2 feet.

The cleaning member is of a flexible material. This is because it is in frictional engagement with the inner surface of the window so as to keep the window clean, i.e., transparent to UV light, by removal of any particles or matter that come to settle on or adhere to the inner surface. The material should thus be sufficiently rigid to remove such materials and flexible or pliable so as not to damage the surface. A material that retains these desirable characteristics over time, so as to minimize the need for maintenance or replacement is thus optimal. A material that retains well its original shape over time is said to have good "memory". Preferably, the material is a thermoplastic material and, conveniently, the material is a planar sheet. A preferred material is a tetrafluoroethylene fluorocarbon polymer, most preferably the material is Teflon™.

The cleaning member is typically in the shape of a blade, the blade having an edge which extends in substantially continuous contact with the interior surface of the cylinder between first and second longitudinal ends of the tube. The blade is dimensioned such that the edge, when the blade is in relaxed condition, extends radially beyond the inner surface of the cylinder so as force the edge into flexed abutment with the curved interior surface of the tube. The blade is preferably a planar sheet of a tetrafluoroethylene fluorocarbon polymer having a thickness of between about 0.02 and about 0.05 inches, or between a about 0.025 and 0.045 inches. The blade of the preferred embodiment is Teflon™. The preferred blade is about 0.03 inches in thickness and is of constant rectangular cross section, when in relaxed condition.

Preferably, an apparatus of the present invention includes a sensor system that provides an indication of proper and/or improper functioning of the apparatus. There is a first UV radiation sensor trained to receive UV radiation from the UV light source which has not been transmitted through the treatment chamber. There is a second UV radiation sensor trained toward the chamber to receive UV radiation emitted from within the chamber. Means for determining the intensities of UV light received by the first and second sensors so as to determine the effectiveness of treatment of liquid within the chamber are also provided.

In the disclosed embodiment, the first sensor is arranged to receive UV light exclusively from the bulb onto which it is trained and the second sensor is arranged to receive UV light from the chamber without receiving any light emitted directly from a bulb.

Preferably, means is also provided to preclude flow of liquid through the apparatus if it is determined that the liquid flowing through the apparatus might not be subject of satisfactory treatment. If the intensity of the UV signal reaching the sensor trained on the bulb is too low, an unsatisfactory condition is indicated. If the intensity of the UV light detected by the sensor trained on the treatment chamber is too low relative to the UV light detected by the sensor trained on the bulb is too low, an unsatisfactory condition is indicated.

It may be found for certain applications, that an indication of an unsatisfactory condition is suitable while in other applications, an automatic cutoff of the water flow is preferred. An indication of an unsatisfactory condition could be a light (LED) signal, an audio signal, an electrical or digitized optical signal to a household control panel, etc. A device having a warning system compatible with Bluetooth™ technology might be desirable.

In a particular aspect, an apparatus of the present invention includes:

a first UV radiation sensor trained to receive UV radiation from the UV light source which has not been transmitted through the treatment chamber;

a second UV radiation sensor trained toward the chamber to receive UV radiation emitted from therewithin; and means for determining the intensities of UV light received by the first and second sensors so as to determine the UV transmittance of water through the treatment chamber.

If the intensity of light received by the second sensor relative to the first sensor is too low, i.e., below a predetermined amount, this means that a relatively large amount of light is being absorbed as the light passes through the treatment chamber. This can indicate that the liquid being treated is too murky for effective treatment to be assured. It might also mean that the cleaner is not operating effectively to clean the window, indicating that maintenance is required.

In another aspect, an apparatus of the invention for treating an aqueous liquid such as water with UV light includes:

a pressurized liquid treatment chamber having an inlet end and an outlet end, the chamber being defined by a window permeable to UV light;

a plurality of UV light sources external of the chamber located to emit light through the window into the chamber to expose liquid within the chamber to the emitted light;

a first sensor located and trained to receive UV light emitted from a first of the UV light sources and which has not emerged from the treatment chamber;

a second sensor located and trained to receive UV light emergent from the liquid chamber; and means for determining the intensity of UV light received by the first sensor relative to the intensity of UV light received by the second sensor so as to determine the effectiveness of the treatment.

There can be an indicator operably connected to the intensity determination means, to provide an indication of when the intensity of UV light received by the first sensor relative to the intensity of UV light received by the second sensor is above a predetermined level.

There can be an indicator operably connected to the first indicator, to provide an indication of when the intensity of UV light received by the first sensor is below a predetermined level.

If the intensity of UV light reaching the first sensor is too low, i.e., below a predtermined amount, this can indicate that light being emitted by the bulb is insufficient to assure adequate treatment of the liquid in the chamber.

The apparatus can include means for precluding flow of said liquid through the treatment chamber, operably connected to a means for determining the intensity of UV light received by the first sensor relative to the intensity of UV light received by the second sensor. A shut-off valve that automatically halts water flow through the apparatus in the case of a possible malfunction of the treatment system can thus be included. It is likely that the valve would be located in-line in advance of the treatment apparatus. This would reduce pressure within the apparatus, and assist in any maintenance operation that requires opening of the treatment chamber.

An apparatus can include UV light sources that are low-pressure mercury lamps. In the disclosed embodiment, the lamps are electrically connected to each other in series.

The treatment chamber, e.g., a quartz tube or hollow cylinder, of the invention preferably can withstand interior liquid pressure of up to about 150 pounds per square inch. The normal pressure range of operation would be between 50 and 140 pounds per square inch, preferably between 50 and 120, or 60 and 100, or 70 and 90, or about 80 pounds per square inch.

A cleaner blade in a preferred aspect of the invention is secured to its shaft along a line parallel to the central axis of a tube, e.g., quartz tube.

In a particular embodiment, the first sensor is trained to directly receive radiation emitted from the first UV light source, and the second sensor is oriented so as not to receive radiation emitted directly from a said light source.

In a preferred apparatus, the window is a quartz sleeve of circular cross section, and the apparatus includes an interior cleaning member having a surface in abutting engagement with an interior surface of the sleeve and moveable with respect thereto for cleaning thereof.

In another aspect, a cleaning member of the invention is mounted on a central shaft so as to be rotatable about a central axis of the sleeve of the treatment chamber, the surface of the cleaning member is in abutting engagement with the interior surface of the sleeve and extends continuously between first and second axial ends of the sleeve, and the member includes a plurality of protrusions located radially intermediate the shaft and the sleeve to promote turbulence of liquid flowing axially through the sleeve.

In another aspect, the invention is a process for treating an aqueous liquid. The process includes passing pressurized liquid through a treatment chamber, the chamber having a window permeable to UV light, an inlet end, and an outlet end. Liquid is treated within the chamber by exposing the liquid to UV light emitted from a UV source external to the chamber. The process includes cleaning an interior surface of the window by turning a shaft located within the chamber, the shaft having a flexible cleaning member affixed thereto, with respect to the window when the member is in flexible engagement with the surface. The shaft includes at least one member extending therefrom so as to disrupt axial flow of water through the chamber from the inlet end to the outlet end.

In a preferred aspect of the method, the window is a cylindrical quartz tube of circular cross section; the shaft extends axially between first and second ends of the tube, and said extending member extends from the shaft toward to the tube a distance equal to at least one quarter the inner diameter of the tube. In the disclosed embodiment, the extending members are wings that protrude radially outwardly from the shaft a distance of about ⅓ the inner diameter of the tube. The distance can be between about ⅕ or ¼ to about ⅜ or 5/11, and to some extent depends upon the diameter of the shaft from which the member extends.

The extending member can have a surface facing the inlet end with the cross-sectional area of the surface being equal to at least 5 percent of the cross sectional area of the tube. Preferably, there are at least two such extending members, and the combined cross-sectional areas of the extending members are equal to at least 30 percent of the cross sectional area of the tube. Increasing the total cross-sectional area of the surfaces and the degree to which the members extend toward the radially outer portion of the chamber increases the amount of disruption of axial flow of liquid through the chamber from its inlet to outlet end.

In a preferred aspect, the total volume of the interior of a quartz tube of the invention is up to about ¼ U.S. gallons, the volume occupied by liquid to be treated, e.g., water is at least 50 percent of the total volume of the tube, and the flow rate of the water through the tube is up to about 20 gallons per minute. Usually, the volume is at least 1/10 of a gallon and it could be 1 or more gallons. In various aspects, the total volume is between 1/10 and 1 gallons, 1/10 and ¾ gallons, 1/10 and ½ gallons and 1/10 and ¼ gallons.

In a preferred aspect, the pressure of the water within the chamber during treatment is between about 60 and 100 pounds per square inch. In other aspects, the pressure is between 30 and 200, 40 and 180, 50 and 160, 60 and 160, 60 and 150, 60 and 130, 70 and 130, 70 and 110, 70 and 100, 70 and 90 pounds per square inch. The operating pressure is often about 80 pounds per square inch plus or minus 10 pounds per square inch.

In another aspect, an apparatus of the invention includes an impeller rotatably responsive to liquid passing through the apparatus and the shaft to which the cleaning blade is affixed is connected to the impeller for rotation thereof. In this way, movement of the liquid, e.g., water through the treatment chamber provides motive force for the cleaning mechanism.

The cleaning member, e.g., Teflon™ blade can be connected to a central shaft rotatably driven about a central axis of a quartz tube that defines a UV-transmissive window of the treatment chamber.

Simply stated, a flexible cleaning member can be a blade extending between the first and second ends of the sleeve, e.g., circular quartz cylinder of the treatment chamber.

A sleeve of the treatment chamber can be a hollow tube of substantially circular cross section, and the ratio of the inner diameter of the tube to the average outer diameter of the shaft can be between about 10:1 and about 3:1, or between about 10:1 and 5:1 or between about 9:1 and 7:1 or about 8:1.

The blade can be of substantially planar Teflon™ having a UV-transmissivity of at least about 15% percent.

There can be an electric motor operably connected to an end of the shaft to drive rotation of the shaft within the treatment chamber.

A preferred window is a quartz tube having a relatively constant thickness of between about 0.05 and 0.25 inches, preferably about 0.12 inches thick. The outer diameter of the quartz tube is typically between about 1.25 inches and about 5.0 inches.

The blade can be fastened along a first linear edge thereof to the shaft and a surface of the cleaning member in abutting engagement with the interior surface of the sleeve can include a second linear edge of the blade, parallel to the first edge. The blade can be of flexible material which is dimensioned such that the second edge of the blade, when the material is in relaxed condition, extends radially beyond the internal radius of the tube so as to force said second edge into flexed abutment with the curved interior surface of the tube.

The apparatus can include a reflector oriented to direct UV radiation emitted from the UV source(s) toward the treatment chamber, e.g., quartz sleeve.

The second sensor can be oriented so as not to receive radiation emitted directly from a UV source, e.g., a lamp.

The apparatus can include means for blocking flow of liquid through the apparatus when the intensity of radiation received by the first sensor is below a predetermined amount. Such means can be a shut-off valve, biased in the closed position, positively maintained in the open position when the intensity of radiation received by the first sensor is not below the predetermined amount.

In a particular mode of operation, there can be a shut-off valve for blocking flow of liquid through the apparatus, biased in a closed position, positively maintained in an open position (i) when the intensity of radiation received by the first sensor is above a predetermined amount and (ii) when the intensity of radiation received by the second sensor relative to the intensity of radiation received by the first sensor is above a predetermined value; and means for maintaining the valve in the open position when the cleaning member is in a position which obstructs receipt of radiation from the UV radiation source by the second sensor. There can be a first indicator for indicating a condition in which the intensity of radiation received by the first sensor is below a predetermined amount. There can be a second indicator for indicating a condition in which the intensity of radiation received by the second sensor relative to the intensity of radiation received by the first sensor is below a predetermined value.

A particular process of the invention for treating an aqueous liquid, includes the steps of:
  passing the liquid under pressure greater than ambient through a treatment chamber;
  exposing the liquid in the treatment chamber to UV light emitted from a UV source through a UV-transmissive wall of the treatment chamber;
  determining the intensity of the UV light emitted from the light source;
  determining the intensity of UV light received by a UV light sensor trained to receive light emerging from the treatment chamber;
  determining whether the treatment has a predetermined effectiveness based on the intensity of the UV light emitted from the light source and the intensity of the UV light received by the sensor.

The treatment chamber can include a tubular quartz housing of circular cross section, and the process further includes the steps of passing water under pressure from one axial end to the other of the housing, and rotating a wiper located within the housing about a central axis of the housing against an interior surface of the housing to clean the surface.

The liquid can be supplied to the apparatus under pressure of a municipal water supply.

An apparatus of the invention can be arranged so as to have a "predetermined effectiveness" in operation. In other words, the number of UV lamps, volume and dimensions of the treatment chamber can be determined such that, so long as the rate of water passing through the apparatus does not exceed a certain amount (i.e., the pressure of the water delivered into the apparatus does not exceed a certain maximum) then the operator can be reasonably assured that water emerging from the apparatus has been suitably treated. The apparatus described in the preferred embodiment, for example, operating with a water flow rate of 40 L/min and a percent transmittance of UV light >75 percent would be produce a UV dose of approximately 80 mJ/cm$^2$.

It will be kept in mind also, that because the sensor array of the preferred embodiment of the present invention, detailed below, includes monitoring the amount of light emerging from liquid subject to treatment, the deleterious effects of turbid water, etc., can also be taken into account in determining the predetermined "shut-off" point of the apparatus.

In the preferred embodiment, the wiper shaft is relatively narrow, i.e., has an effective diameter that is about 23 percent of the inner diameter of the quartz housing of the treatment chamber. It will be appreciated that the narrower the shaft, the greater the amount of light distributed throughout the interior of the treatment chamber. In the preferred embodiment, the ratio of the chamber diameter to the shaft diameter is about 4:1. Increasing this ratio would generally increase the effectiveness of the UV light to which the liquid being treated is exposed. A ratio of 10:1 or greater may be achievable, but a ratio as small as 2:1 may still obtain a result that is satisfactory in a particular context. Of course, there is a maximum to the ratio, as the structural integrity of the shaft must be maintained and there is thus a minimum effective diameter of the shaft that must be maintained.

Members affixed with respect to the shaft of the treatment chamber extend radially outwardly into the chamber and provoke turbulence of the liquid flowing through the treatment chamber. This arrangement, which permits inclusion of a relatively narrow shaft as part of a treatment apparatus, permits the usable volume of the treatment chamber to increased. Preferably, an apparatus of the present invention includes a shaft, wiper blade and turbulence inducing members that together take up no more than about 10 or 11 percent of the total volume of the treatment chamber. This leaves about 89 or 90 percent of the total volume of the chamber free to be occupied by liquid to be treated.

An important feature of the preferred embodiment of the present invention is the sensor arrangement. The arrangement provides two functions. A first of the functions is to indicate failure of the UV source. Thus the sensor that is arranged to detect light that has not been subject to the absorbing effects of the liquid in the treatment chamber can be used to provide an indication of when light being emitted from the UV source is insufficient for assured effectiveness of the apparatus. Generally, this sensor is trained directly on the UV source, although it could receive light indirectly via a reflector of some sort, if this was to be advantageous under particular circumstances. A second of the functions is to determine that the amount of light being received within the treatment chamber is sufficient for assured effectiveness of the apparatus. Generally, this function is achieved by use of second sensor that is trained to receive light that has travelled through the treatment chamber and the intensity of the emergent light is used as an indication of whether the treatment is effective. Generally, if the intensity of emergent light is found to be less than a predetermined amount, an indication is given that an "unsafe" condition may be present. Of course, the apparatus can be provided with an automatic shutoff that would be activated under such a circumstance. The reason for an insufficiently low level of emergent light to come about could be because of a malfunction of the UV light source, turbidity of the liquid within the chamber, etc.

The particular apparatus disclosed herein is designed to operate with the UV lamps on at all times, regardless of whether water is flowing through the quartz tube. It may be advantageous to provide the apparatus with means for turning the lamps off or lowering the power thereto when there is no liquid flow. Such an arrangement could save on power costs and extend lamp life, but care should be taken to ensure that all liquid flowing through the quartz tube is adequately treated.

An apparatus of the present invention also includes means for driving the wiping mechanism. Such a means may be an impeller, where liquid flow itself propels movement of the wiper, or an electric motor could be used. Any suitable means could be provided by a skilled person.

BRIEF DESCRIPTION OF THE DRAWINGS

For a more complete understanding of the present invention, the following description is given which makes reference to the accompanying drawings in which.

DESCRIPTION OF PREFERRED EMBODIMENTS

Figure 1:
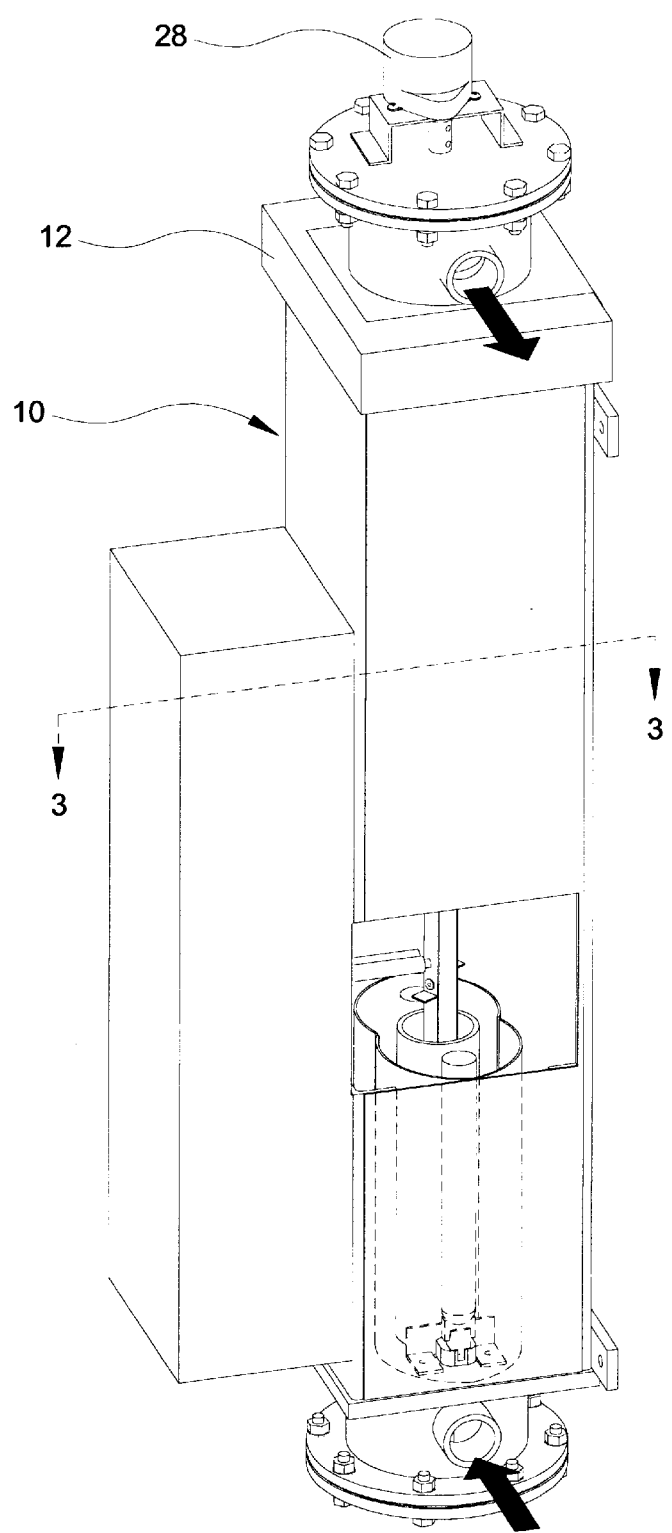
FIG. 1 is a perspective view of a household point-of-entry UV water treatment unit, there being a partial cutaway of the unit housing to expose inner workings thereof.

Turning to the drawings, FIG. 1 shows the exterior of a typical point-of-entry unit 10 of the present invention. This point-of-entry unit is generally installed in-line in a pressurized household water system. A pipe from the municipal water supply is thus connected by any suitable means at the lower end of the unit and a pipe leading to the household distribution system is connected at the upper end of the unit.

The precise location of the unit within the household water distribution system is optional. As a point-of-entry unit, it would generally be located in-line between the household water source and the household distribution system. The water source would be the water as provided from a municipal system, or it could be from an underground well, etc. As such, all water provided through the household distribution system would be subject to treatment by the unit. It may be that a particular user would prefer to have only water to be consumed subject to treatment, so as to enhance economies of use of the unit. It would thus be possible, for example, to locate the unit under the kitchen sink, so as to subject only the water provided through a dedicated kitchen faucet to UV-treatment by the unit.

In FIG. 1 is illustrated unit 10 which includes housing 12. Because of the possible damaging effects UV radiation can have to the human eye, housing 12 is of UV-nontransmissive material and the arrangement provides to substantially preclude any leakage of UV radiation therefrom. Further, the housing should be provided with a mechanism which automatically shuts off all UV bulbs located therein upon opening of the housing. The details of connecting unit 10 in-line to a water piping system are not illustrated as a person skilled in the art would be readily able to provide such connecting means.

Figure 2:
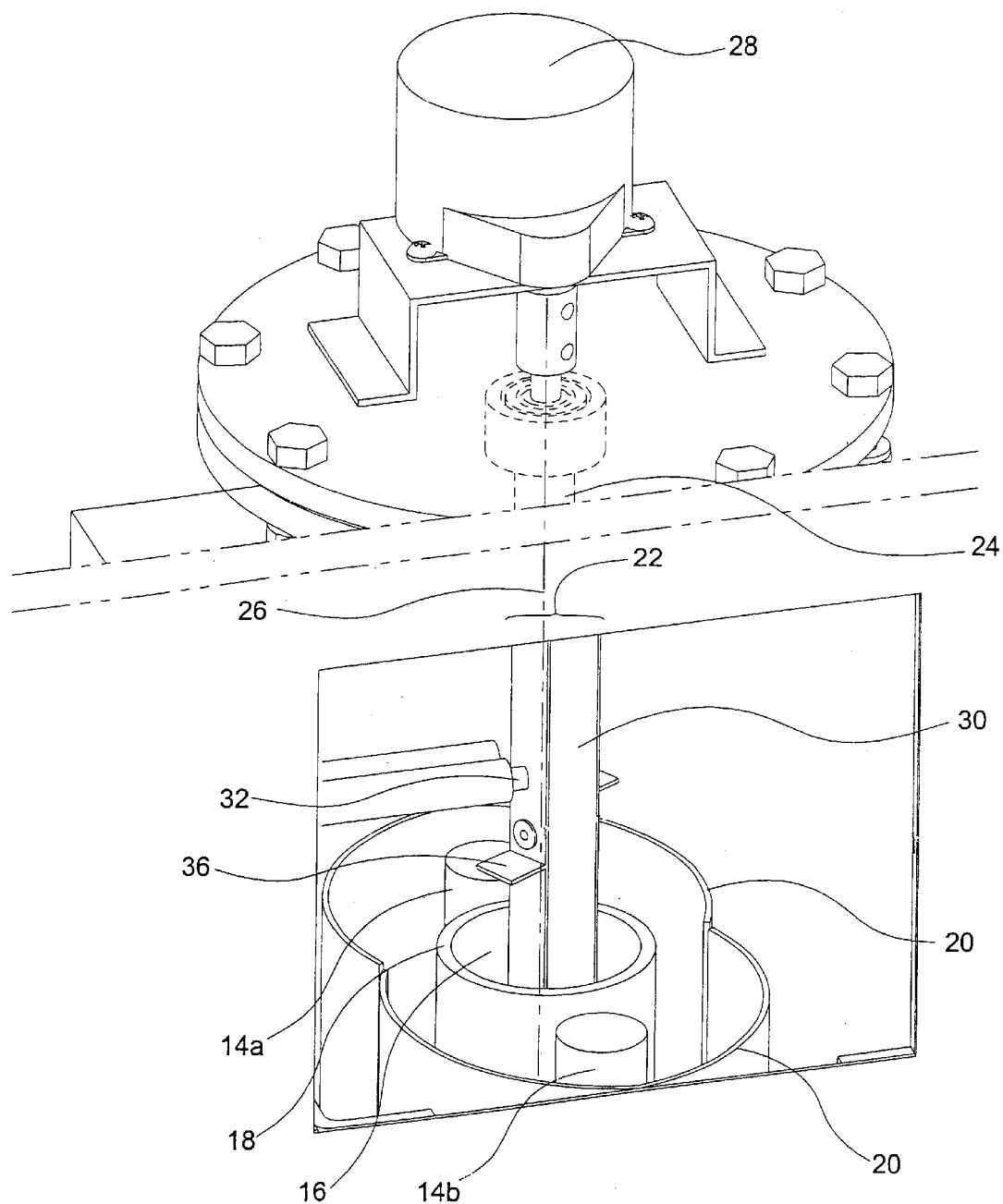
FIG. 2 is an enlargement of the cutaway view of FIG. 1.

As seen in FIG. 2, the illustrated embodiment includes two UV bulbs 14a, 14b. Each bulb is about 24 inches (about 60 cm) in length, 60 watts in power and provides 20 watts in energy at 254 nm. Bulbs known in the United States and Canada as high output-low pressure bulbs and available from Light Sources Inc. of Connecticut are generally suitable. The UV bulbs are located externally of the water treatment chamber 16, the side walls of which are provided by a single quartz tube 18. The lamps are axially parallel to the quartz tube of the treatment chamber and thus generally parallel to the vectorial direction of flow of the water being treated. Quartz tubing is used as it is transmissive to UV radiation emitted from bulbs 14a, 14b and so liquid water contained in the treatment chamber can h be exposed to the UV radiation.

Quartz tube 18 has an inner diameter of about 1.6 inches (about 4 cm) and is about 2 feet (about 60 cm) in length. The wall is about 0.118 inches (about 0.3 cm) thick. Such a tube can withstand internal (expansive) pressures of up to about 150 psi (pounds per square inch) which renders it compatible for use with most, if not all, municipal water systems in the United States and Canada.

In order to enhance the proportion of UV radiation emitted from bulbs 14a, 14b that is directed toward the interior of the treatment chamber, the treatment unit includes reflectors 20. These reflectors are shaped as illustrated, and preferably so as to optimize the amount of UV light reaching the interior of the treatment chamber. The patent literature describes reflectors and the advantages attendant with use of reflectors. See, for example U.S. Pat. No. 5,247,178 of Ury et al., which issued on Sep. 21, 1993.

The water being treated by a unit according to the present invention typically contains impurities, which can be of the desirable and/or undesirable type. Thus such water can contain minerals such as sodium, calcium, iron, and/or fluoride, for example. Impurities can, over time, lead to build up of deposits on the interior of the quartz tube and this leads to a decrease in the light-transmissive capacity of the tube, and particularly to a reduction in the UV radiation transmissive capacity. At least to the extent that such deposits can lead to a decrease in the efficiency of a treatment device, it is desirable to remove such deposits. There have been various approaches taken in the art to dealing with such deposits. In the case of the preferred embodiment of the present invention, an approach which is effective without requiring any special effort on the part of the user is desirable.

Unit 10 thus includes cleaning apparatus 22. Apparatus 22 includes central shaft 24, which is centered on (i.e., is coaxial with) the central axis 26 of tube 18. Located within the top end of housing 12 is motor 28 connected to shaft 24 so as to cause rotation of the shaft about the central axis of the tube. Locating the motor at the top of the apparatus advantageously reduces the possibility of water reaching the motor in the case of a leak. Locating the motor at the bottom of the apparatus can improve installation and maintenance characteristics of the apparatus. For example, bulb replacement can be more convenient when the motor is located at the bottom of the apparatus. The electric motor is any suitable conventional motor and the motor generally operates to provide rotation of the shaft at a rate of about 60 revolutions per hour. Affixed to the shaft is wiper 30. Wiper 30 is a single piece of Teflon™ 0.03 inches in thickness, but it can be made up of multiple pieces of Teflon™ layered together. The wiper is of sufficient thickness and flexibility to have 30 inch-ounces torque. Wiper 30 is fastened to shaft 24, which shaft is a stainless steel bar. The wiper is affixed to the bar by nuts and bolts, rivets, or any other suitable fasteners. In the illustrated embodiment, the radius of the wiper, when in unflexed condition, extends about 0.08 inches (about 0.2 cm) radially outwardly beyond the inner circumference of the circle coincident with the inner surface of quartz tube 18. In this way, when installed within the tube, the wiper is constantly biased into abutting contact with the interior surface of the tube. In that it is desirable that the wiper edge be constantly biased against the interior surface of the tube so as to retain its cleaning power, it is desirable that the material from which the wiper is manufactured have good "memory" over the expected lifetime of the wiper. In other words, it is desirable that the material be such that it retains its preference for taking a planar shape rather than the slightly bowed shape that it is forced into when installed as part of the unit.

Figure 3:
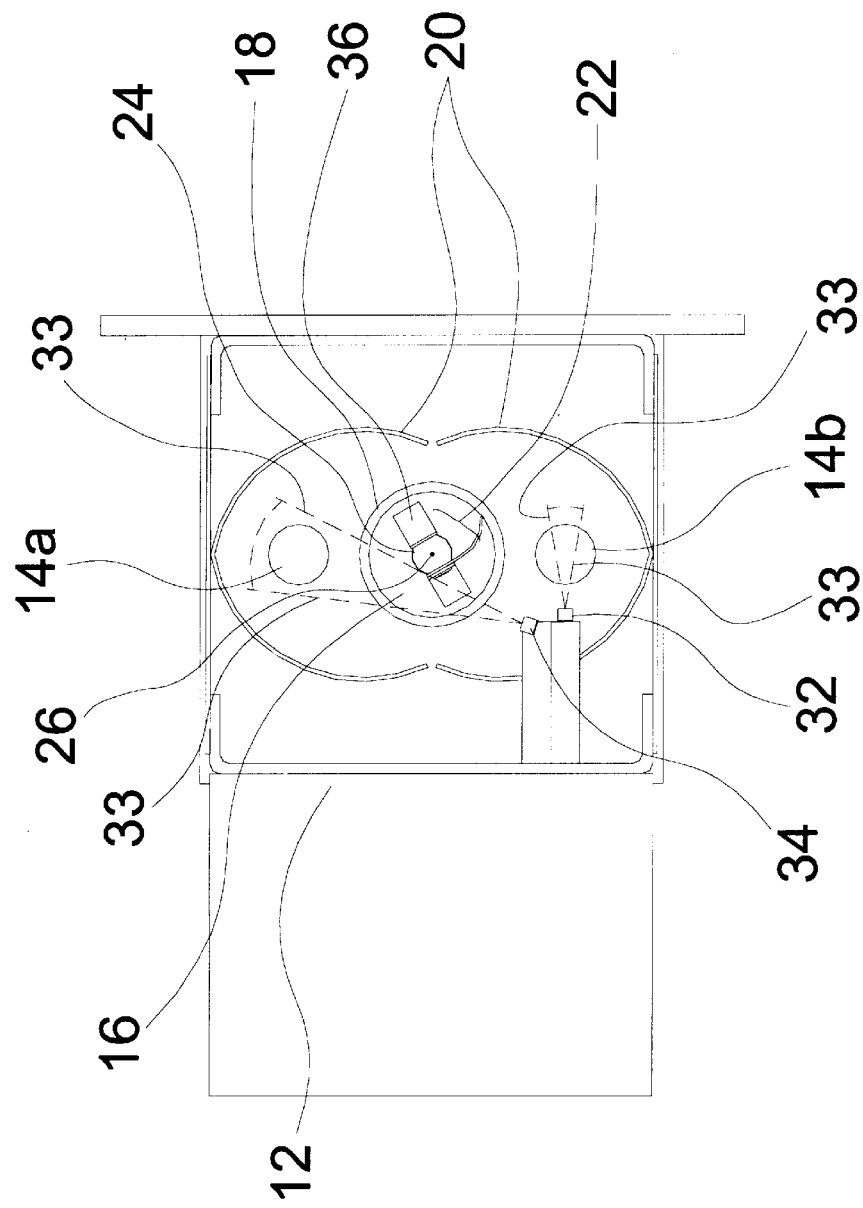
FIG. 3 is a cross-sectional type view of the FIG. 1 unit taken along line 3—3 of FIG. 1.

Stainless steel tabs, or wings, 36 are attached to shaft 24. The wings are rigid in comparison to the flexible cleaning blade and create turbulence in liquid flowing through the treatment chamber. Each wing thus divert liquid flowing through the chamber from its axial flow path when liquid comes into contact with the surface of the wing facing the inlet end of the quartz tube. As can be seen in FIG. 3, each wing 36 presents a surface area transverse to the flow of water that is about 8 percent of the cross sectional area of the cylinder. In particular, the cross-sectional area of the cylinder is about 12.6 cm$^2$ and the surface area of each wing is about 1.0 cm$^2$. In the disclosed embodiment, there are 3 pairs of wings, the pairs being axially spaced apart along the shaft with 7.6 inches between neighboring pairs. The wings of each pair of wings are angularly spaced from one another. A first wing of a pair is located at rotation angle of 180° (with respect to the shaft) with respect to the second wing of the pair.

In that virtually any surface within the treatment chamber that is exposed to water being treated will experience build-up of some material or other from water impurities, it is desirable that the arrangement provide for cleaning of the entire length of the interior of the quartz tube so as to minimize diminution of its UV-transmissive property over time. To this end, the wiper blade of the illustrated embodiment in abutment with the interior tube surface extends the length of the quartz tube, from one end to the other. In this way, one sweep of the wiper of the preferred embodiment provides for a wiping of the entire interior surface of the tube.

Undesirable build-up of materials on the quartz tube to the point that it affects the efficiency of the apparatus generally occurs slowly, i.e., taking a few hours to several or more days of operation in a typical household. The illustrated cleaner, if it were to provide for a single swipe with the passage of every 20 litres of water through the treatment chamber would probably be satisfactory in most circumstances. It must be kept in mind though, that the amount and type of build-up will vary with the impurities contained in the water being treated.

Figures 4, 5:
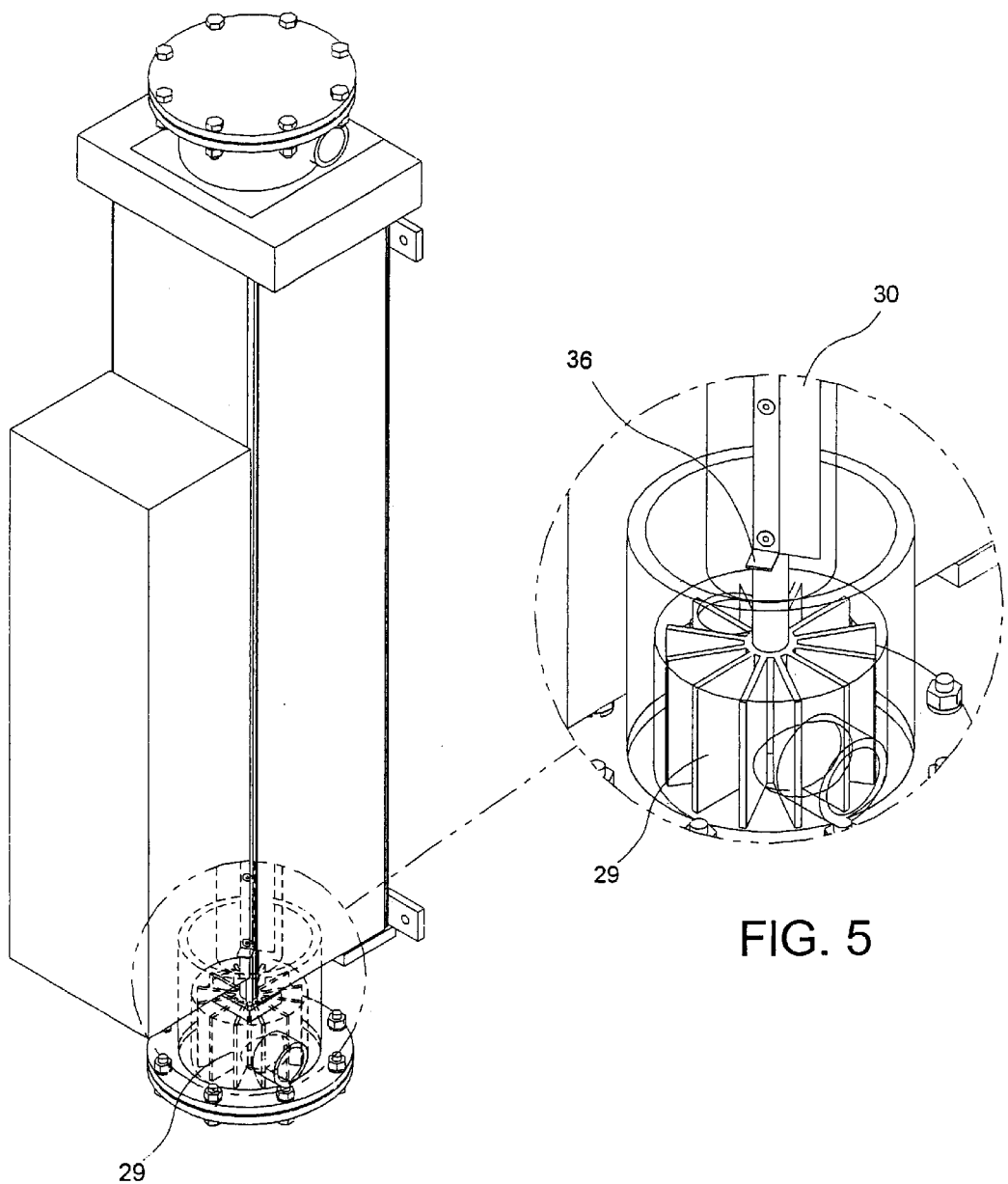
FIG. 4 is a second perspective view of the treatment unit, there being a partial cutaway of the unit housing to expose an impeller.
FIG. 5 is an enlargement of the cutaway view of FIG. 4.

The apparatus illustrated in FIGS. 1 to 3 provides for a cleaner that is driven by an electric motor. It is possible to avoid the need for a motor by providing a an impeller 29, as illustrated in FIGS. 4 and 5, that would force the shaft to rotate as water passes through the impeller and into, as illustrated, (or out of) the treatment chamber. A drive mechanism could also be provided by a handle that extends out of a longitudinal end of the unit and that is connected to the shaft so as to permit manual rotation thereof by a user. As mentioned above, however, it is preferable to have a system that does not rely upon routine intervention of an operator for operation of the cleaner.

It is important to be able to determine the effectiveness of a water treatment apparatus. Clearly, it is desirable that a dose of UV radiation sufficient to render pathological bacteria that may be contained in the water harmless reach all portions of the water being treated.

Figure 6:
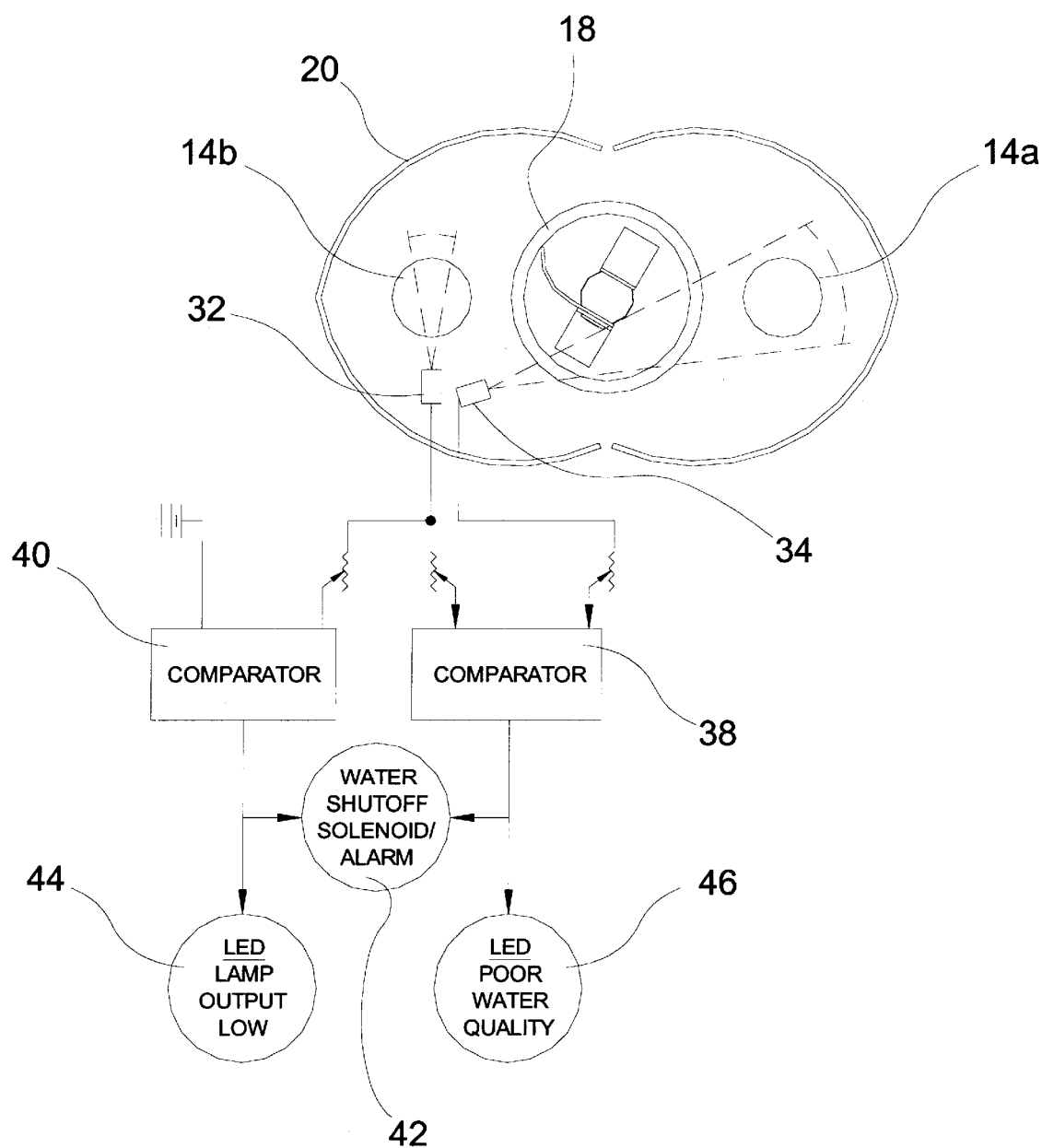
FIG. 6 is a schematic illustrating a sensor arrangement of the invention.

The illustrated water treatment apparatus includes a sensor arrangement, illustrated primarily in FIG. 6, intended to monitor the effectiveness of the treatment being provided by the apparatus. It is thought by the inventors that it is most desirable that the monitoring apparatus be operated at all times that the device is operational, i.e., when the UV lights are activated, but it may be acceptable to others to operate the monitoring system intermittently.

The sensor arrangement of the illustrated apparatus includes sensors 32, 34. (Sensor arrangements for UV apparatuses that treat liquids at ambient pressure are described in international patent application No. PCT/CA99/00435, published under WO 99/58453 on Nov. 18, 1999, and documents referred to therein.) Each of sensors 32, 34 detects UV light incident upon it. Suitable sensors are silicon carbide photodiodes having a spectral range of 210 to 380 nm (Part # JECO.IS of Boston Electronics Corp., Brookline Mass. The outer limit of the cone within which incidence light can be received by each sensor is shown by lines 33. Sensor 32 is trained directly on UV bulb 14b. Sensor 32 thus detects UV light that is emitted from bulb 14b that has not been transmitted through the treatment chamber.

Sensor 34 is trained on the treatment chamber and in particular is directed away from bulb 14a such that substantially all UV light that the sensor is capable of detecting is radiation that is emergent from the treatment chamber through the quartz tube defining the treatment chamber.

In the illustrated embodiment, UV bulbs 14a, 14b are electrically connected in series and so they produce UV radiation of roughly the same intensities.

Sensors 32, 34 are calibrated and adjusted by means of an adjustable resistor connected in parallel with each sensor such that the relative intensities of the UV light being received by each sensor can be determined. The system includes comparator 38 so that if the intensity of UV radiation being detected by sensor 32 is too great with respect to the intensity of UV radiation being detected by sensor 34, i.e., the relative intensities are such that the effectiveness of the treatment cannot be assured, a signal is sent to a shut-off valve 42 which halts the flow of water through the apparatus. This automatic shut-off arrangement is not illustrated any further because such an arrangement is conventional in the art and the skilled person would be readily able to construct such. It is thought by the inventors, however, that a shut-off valve that is biased toward its closed position and is positively held in its open position when the system is operating effectively is preferred. In this way, any type of malfunction that leads to an unacceptable operating condition between the two sensors, and thus to an absence of positive signal to the valve, will lead to valve closure. A manual override can in turn be included to defeat the shut-off valve to permit the flow of water when the apparatus is not functioning. In this way, water (although untreated by the apparatus) could still be made available during a power outage, for example.

The system includes comparator 40 connected to sensor 32. When light being detected by sensor 32 falls below a certain amount a bulb malfunction or failure is detected. Again, in response to this fault condition, flow of water is halted through closing of valve 42.

In response to a fault condition, it is also possible to include audio or other type of alarm, such as LEDs 44, 46 that can indicate to the user the existence of the fault condition.

In the illustrated embodiment, there are two bulbs, electrically connected in series, as described above. It is within the scope of the present invention that a system with only one bulb, or with more than two bulbs could be devised by a skilled person. In a system having only one UV bulb as a source of UV radiation, the sensor 34 trained to receive radiation emergent from the treatment chamber could be located on the generally opposite of the tube to that of sensor 32.

It will be apparent that sensor 34 is situated so as to receive light rays emitted from bulb 14a and that are non-diametrical with respect to a circle generally coincident with the quartz tube. This is because shaft 24 of the cleaner is located in the center of the tube and so would obstruct passage of such diametrical light rays. It will be appreciated that the light rays shown in FIG. 3 are illustrative and refractive effects of the quartz tube on the radiation transmitted therethrough are ignored.

It will also be apparent that as the wiper rotates about shaft 24, the wiper is periodically brought into a position in which it obstructs the passage of light rays from bulb 14a through the treatment chamber to sensor 34. This condition defeats the operation of the monitoring system as the wiper turns. To take this into account, the signal received by sensor 34 is electronically conditioned to remove the peak signals received as the wiper rotates.

It may be desirable to include apertures in wiper 30. Such apertures could be arranged to permit transmission of radiation from both bulbs that would otherwise be interfered with by the wiper into other portions of the treatment liquid, thereby increasing the effectiveness of the treatment. An aperture could also reduce the "down time" of the sensors by being located so as to permit light from bulb 14a to reach sensor 34 when the wiper is located directly in line between the bulb and sensor. Such apertures could also increase the amount of turbulence of the water flowing through the treatment chamber enhancing the effectiveness of the treatment. Care would have to be taken to maintain the structural integrity of the flexible wiper blade, however, so there is certainly a limit as to the size and number of such apertures, if any, that could be included in the wiper blade.

Results obtained through the operation of the illustrated device are given in Table 1, and these establish the feasibility of the treating water with the device. The results indicated are according to NSF (National Sanitation Foundation) Standard 55, including a maximum rated operating pressure of 100 psi, a rated service flow of 10 gpm (gallons per minute).

TABLE I

| Time | Influent | Effluent 1 | Effluent 2 | Log Reduction | Pass/Fail |
|---|---|---|---|---|---|
| Day 1, Hr 0 | $8.00 \times 10^4$ | <1 | <1 | 4.93 | Pass |
| Day 1, Hr 4 | $1.05 \times 10^4$ | <1 | <1 | 5.02 | Pass |
| Day 2, Hr 0 | $7.00 \times 10^4$ | 1 | <1 | 4.85 | Pass |
| Day 2, hr 4 | $6.00 \times 10^4$ | <1 | 2 | 4.78 | Pass |
| Day 3, Hr 0 | $6.08 \times 10^4$ | 5 | 4 | 4.83 | Pass |
| Day 3, Hr 4 | $5.40 \times 10^4$ | 3 | <1 | 4.73 | Pass |
| Day 4, Hr 0 | $5.30 \times 10^4$ | 3 | 10 | 4.72 | Pass |
| Day 4, hr 4 | $7.70 \times 10^4$ | 3 | 4 | 4.87 | Pass |
| Day 7, Hr 0 | $6.80 \times 10^4$ | 3 | <1 | 4.83 | Pass |
| Day 7, Hr 4 | $5.30 \times 10^4$ | <1 | <1 | 4.72 | Pass |
| Day 8, Hr 0 | $4.90 \times 10^4$ | 2 | <1 | 4.69 | Pass |
| Day 8, hr 4 | $5.20 \times 10^4$ | 2 | 1 | 4.72 | Pass |
| Day 9, Hr 0 | $5.10 \times 10^4$ | 2 | <1 | 4.71 | Pass |
| Day 9, Hr 4 | $9.00 \times 10^4$ | <1 | <1 | 4.95 | Pass |

The log reduction at 38,000 mJ/cm2 was 2.57 and this is the passing criteria for the test organism MS2.

Preferably, water is treated according to the invention to meet NSF Standard 55.

All documents referred to in this specification are incorporated herein by reference as though the each documents were reproduced herein in its entirety.

What is claimed is:

1. An apparatus for treating a pressurized liquid, the apparatus comprising:
    a pressurized liquid treatment chamber having an inlet end and an outlet end, the chamber having a window permeable to UV light;
    a UV light source external of the chamber located to emit light through the window into the chamber to expose liquid within the chamber to the emitted light;
    a shaft which extends between the inlet end and the outlet end of the chamber, located to turn about a central axis of the chamber extending between the inlet end and the outlet end;
    a flexible cleaning member affixed to the shaft and extending radially therefrom to flexibly engage an interior surface of the window for cleaning thereof as the shaft turns; and
    at least one member extending radially from the shaft into the treatment chamber to disrupt axial flow of liquid through the chamber.

2. The apparatus of claim 1, wherein:
    the window comprises a hollow cylinder of circular cross section; and
    the volume of the treatment chamber free to be occupied by the pressurized liquid is at least 50 percent of the total volume of the cylinder.

3. The apparatus of claim 2 wherein the member has a surface transverse to the axis, an obverse face of the surface facing the inlet end of the chamber and having a cross sectional area equal to at least 5 percent of the area of the cross section of the cylinder.

4. The apparatus of claim 3 wherein there is a first pair of said members, angularly spaced from each other and axially located nearer to the inlet end of the cylinder than to the center of the cylinder, a second pair of said members, angularly spaced from each other and axially located nearer to the center of the cylinder than to either of the inlet or outlet ends of the cylinder, and a third pair of said members, angularly spaced from each other and axially located nearer to the outlet end of the cylinder than to the center to of the cylinder.

5. The apparatus of claim 3, wherein the member is located nearer the inlet end of the chamber than the outlet end.

6. The apparatus of claim 5, further comprising a second said member, the first and second members being spaced apart angularly from each other.

7. The apparatus of claim 5, further comprising a second said member, the first and second members being spaced apart axially from each other.

8. The apparatus of claim 7, wherein there is a third said member, the third member being spaced angularly apart from the first member.

9. The apparatus of claim 7, wherein the combined said cross sectional areas of the obverse faces of the members is at least 40 percent of said area of cross section of the cylinder.

10. The apparatus of claim 9, wherein the volume of the interior volume of the cylinder is between about 25 and 200 cubic inches.

11. The apparatus of claim 10, wherein the inner diameter of the cylinder is between about 1 and 3 inches.

12. The apparatus of claim 11, wherein the length of the cylinder is between about 6 inches and about 3 feet.

13. The apparatus of claim 12, wherein said flexible member comprises a thermoplastic material.

14. The apparatus of claim 13, wherein said thermoplastic material is a planar sheet of a tetrafluoroethylene polymer.

15. The apparatus of claim 13, wherein the cleaning member comprises a flexible blade having an edge which extends in substantially continuous contact with the interior surface of the cylinder between first and second longitudinal ends of the cylinder.

16. The apparatus of claim 15, wherein the blade is dimensioned such that said edge, when the blade is in relaxed condition, extends radially beyond the inner surface of the cylinder so as to force the edge into flexed abutment with the curved interior surface of the cylinder.

17. The apparatus of claim 16, wherein the blade comprises a planar sheet of a tetrafluoroethylene polymer having a thickness of between about 0.02 and about 0.05 inches.

18. The apparatus of claim 2, further comprising:
a first UV radiation sensor trained to receive UV radiation from the UY light source which has not been transmitted through the treatment chamber;
a second UV radiation sensor trained toward the chamber to receive UV radiation emitted from therewithin; and
means for determining the intensities of UV light received by the first and second sensors so as to determine the effectiveness of treatment of liquid within the chamber.

19. The apparatus of claim 2, further comprising:
a first UV radiation sensor trained to receive UV radiation from the UV light source which has not been transmitted through the treatment chamber;
a second UV radiation sensor trained toward the chamber to receive UV radiation emitted from therewithin; and
means for determining the intensities of UV light received by the first and second sensors so as to determine the UV transmittance of liquid through the treatment chamber.

20. An apparatus for treating an aqueous liquid such as water with UV light, the apparatus comprising:
a pressurized liquid treatment chamber having an inlet end and art outlet end, the chamber being defined by a window transmissive to UV light,
a plurality of UV light sources external of the chamber located to emit light through the window into the chamber to expose liquid within the chamber to the emitted light;
a first sensor located and trained to receive UV light emitted from a first of the UV light sources and which has not emerged from the treatment chamber;
a second sensor located and trained to receive UV light emergent from an opposite side of the liquid chamber; and
means for determining the intensity of UV light received by the first sensor relative to the intensity of UV light received by the second sensor so as to determine the effectiveness of the treatment.

21. The apparatus of claim 20, further comprising an indicator operably connected to said means, to provide an indication of when the intensity of UV light received by the first sensor relative to the intensity of UV light received by the second sensor is above a predetermined level.

22. The apparatus of claim 20, further comprising an indicator operably connected to the first sensor to provide an indication of when the intensity of UV light received by the first sensor is below a predetermined level.

23. The apparatus of claim 20, further comprising means for precluding flow of said liquid through the treatment chamber, operably connected to said means for determining the intensity of UV light received by the first sensor relative to the intensity of UV light received by the second sensor.

24. The apparatus of claim 20, wherein each of said UV light sources comprises a low-pressure mercury lamp and the lamps are electrically connected to each other in series.

25. The apparatus of claim 15, wherein:
said cylinder can withstand interior liquid pressure of up to about 150 pounds per square inch;
said UV light source is a low-pressure mercury vapor bulb; and
the blade is secured to the shaft along a line parallel to the central axis of the cylinder.

26. The apparatus of claim 20, wherein the first sensor is trained to receive radiation emitted directly from the first UV light source, and the second sensor is oriented so as not to receive radiation emitted directly from a said light source.

27. The apparatus of claim 20, wherein the window comprises a quartz sleeve of circular cross section, and further comprising an interior cleaning member having a surface in abutting engagement with an interior surface of the sleeve and moveable with respect thereto for cleaning thereof.

28. The apparatus of claim 27, wherein said cleaning member is mounted on a central shaft so as to be rotatable about a central axis of the sleeve, the surface of the cleaning member in abutting engagement with the interior surface of the sleeve extends continuously between first and second axial ends of the sleeve, and the member includes a plurality of protrusions located radially intermediate the shaft and the sleeve to promote turbulence of liquid flowing axially through the sleeve.

29. A process for treating an aqueous liquid, the process comprising the steps of:
passing liquid under pressure through a treatment chamber, the chamber having a window permeable to UV light, an inlet end, and an outlet end;
treating the liquid within the chamber by exposing the liquid to UV light emitted from a UV source external of the chamber; and
cleaning an interior surface of the window by turning a shaft located within the chamber, the shaft having a flexible cleaning member affixed thereto, with respect to the window when the member is in flexible engagement with the surface; wherein:

the shaft includes at least one relatively rigid member extending therefrom, so as to disrupt axial flow of the liquid through the chamber from the inlet end to the outlet end.

30. The method of claim 29, wherein the window is a cylindrical quartz tube of circular cross section; the shaft extends axially between first and second ends of the tube, and said extending member extends radially from the shaft toward to the tube a distance equal to at least one quarter the inner diameter of the tube.

31. The method of claim 30, wherein, the extending member has a surface facing the inlet end, the cross-sectional area of which surface is equal to at least 5 percent of the cross sectional area of the tube, there are at least two said extending members, and the combined cross-sectional areas of the said extending members are equal to at least 30 percent of the cross sectional area of the tube.

32. The method of claim 31, wherein the total volume of the interior of the tube is up to about ¼U.S. gallons, the volume occupied by the liquid is at least 50 percent of the total volume, and the flow rate of the liquid through the tube is up to about 20 gallons per minute.

33. The method of claim 32, wherein the pressure of the liquid within the chamber is between about 60 and 100 pounds per square inch.

* * * * *